United States Patent
He et al.

(10) Patent No.: US 8,728,756 B2
(45) Date of Patent: *May 20, 2014

(54) PROMOTING AXON REGENERATION IN THE ADULT CNS THROUGH CONTROL OF PROTEIN TRANSLATION

(71) Applicant: Children's Medical Center Corporation, Boston, MA (US)

(72) Inventors: Zhigang He, Wellesley, MA (US); Kevin Park, Boston, MA (US); Kai Liu, Kowloon (HK); Yang Hu, Brookline, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/729,091

(22) Filed: Dec. 28, 2012

(65) Prior Publication Data

US 2013/0123228 A1     May 16, 2013

Related U.S. Application Data

(63) Continuation of application No. 12/479,805, filed on Jun. 6, 2009, now Pat. No. 8,367,352.

(60) Provisional application No. 61/059,568, filed on Jun. 6, 2008.

(51) Int. Cl.
 *C12Q 1/02* (2006.01)
 *A61K 49/00* (2006.01)

(52) U.S. Cl.
 USPC .............................. 435/29; 424/9.1

(58) Field of Classification Search
 USPC .................................... 435/29, 9.1
 See application file for complete search history.

(56) References Cited

U.S. PATENT DOCUMENTS

2007/0292532 A1   12/2007   Woscholski et al.

FOREIGN PATENT DOCUMENTS

| WO | 2004/075897 | 9/2004 |
|---|---|---|
| WO | 2005/054257 A1 | 6/2005 |
| WO | 2005/097119 | 10/2005 |
| WO | 2007/094755 | 8/2007 |

OTHER PUBLICATIONS

Zhang et al. Critical Role of PTEN in the Coupling Between PI3K/AKT and JNK1/2 Signaling in Ischemic Brain Injury; FEBS Letters, vol. 581 (2007) pp. 495-505.*
Park et al., Science, 322:963-966 (2008). "Promoting Axon Regeneration in the Adult CNS by Modulation of the PTEN/mTOR Pathway."
Cohen-Cory et al., Nature, 378:192-196 (1995). Effects of brain-derived neurotrophic factor on optic axon branching and remodelling in vivo.
Weibel et al., Brain Research, 679:249-254 (1995). "Brain-derived neurotrophic factor (BDNF) prevents lesion-induced axonal dieback in young rat optic nerve.".
Arevalo et al., Molecular Biology of the Cell, 17:3369-77 (2006). "Activation of casein kinase II and inhibition of PTEN."
Chang et al., Trends in Neuroscience, 30(11):581-586 (2007). "Phosphatase PTEN in neuronal injury and brain disorders."
Koprivica et al., Science, 310:106-110 (2005). "EGFR activation mediates inhibition of axon regeneration by myelin and chondroitin sulfate proteoglycans."
Peng et al., European Journal of Neuroscience, 25(5):1332-1340 (2007). "Protein tyrosine phosphatase inhibition reduces degeneration of dopaminergic substantia nigra neurons and projections in 6-OHDA treated adult rats."
Rickle et al., Journal of Neuroscience Research, 84(3):596-605 (2006). "PTEN, Akt, and GSK3 beta signaling in rat primary cortical neuronal cultures following tumor necrosis factor-alpha and trans-4-hydroxy-2-nonenal treatments."
Schmid et al. FEBS Letters, 566:35-38 (2004). "Bisperoxovanadium compounds are potent PTEN inhibitors."
Zhu et al., Neurochemistry International, 50(3):507-516 (2007). "Implication of PTEN in production of reactive oxygen species and neuronal death in in vitro models of stroke and Parkinson's disease."
Araki et al., Science, 305:1010-1013 (2004). "Increased nuclear NAD biosynthesis and SIRT1 activation prevent axonal degeneration."
Leon et al., The Journal of Neuroscience, 29(12):4615-4626 (2000). "Lens injury stimulate axon regeneration in the mature rat optic nerve."

* cited by examiner

*Primary Examiner* — Susan Hanley
*Assistant Examiner* — Paul Martin
(74) *Attorney, Agent, or Firm* — David S. Resnick; Shayne Y. Huff; Nixon Peabody LLP

(57) ABSTRACT

Survival of, or axon regeneration in a lesioned mature central nervous system (CNS) neuron is promoted by (a) contacting the neuron with a therapeutically effective amount of an exogenous activator of protein translation; and (b) detecting the resultant promotion of the survival of, or axon regeneration in the neuron.

10 Claims, No Drawings

PROMOTING AXON REGENERATION IN THE ADULT CNS THROUGH CONTROL OF PROTEIN TRANSLATION

CROSS-REFERENCE TO RELATED APPLICATIONS

This application is a continuation application of U.S. patent application Ser. No. 12/479,805 filed on Jun. 6, 2009, which issued as U.S. Pat. No. 8,367,352 on Feb. 5, 2013, which claims benefit under 35 U.S.C. §119(e) of U.S. Provisional Application No. 61/059,568 filed Jun. 6, 2008, the contents of which are incorporated herein by reference in their entireties.

GOVERNMENT SUPPORT

This invention was made with government support under grant P030-HD18655 awarded by the National Institutes of Health. The government has certain rights in the invention.

BACKGROUND OF THE INVENTION

The field of the invention is activating protein synthesis to promote regeneration of a lesioned CNS axon and compensatory regrowth of a spared axon in the mature CNS.

Axon regeneration failure following injury in the adult mammalian CNS has been attributed mainly to two properties of the adult CNS, namely the inhibitory extrinsic environment and diminished intrinsic regenerative capacity of mature CNS neurons (1-5). Numerous studies on the non-permissive environment have led to the identification of a number of molecular players and signaling pathways involved in limiting axon regrowth. While these mechanisms clearly represent important extrinsic barriers for axon regeneration, the strategies to neutralize these inhibitory activities only allowed a limited degree of axon regeneration in vivo (6, 7). Indeed, a permissive environment, such as a sciatic nerve graft transplanted to the lesion site, allows a small percentage of injured adult axons to regenerate (5, 8). These results indicate that neutralizing inhibitory activity is not sufficient and therefore other mechanisms, such as those controlling the intrinsic axonal regenerative potential of neurons, may play an important role in axon regeneration.

In contrast to the axon growth during embryonic development, little is known about the molecular mechanisms that control the intrinsic regenerative ability of adult CNS neurons (1, 3-5, 9). It is also unknown whether similar or different mechanisms operate axon growth during development and axon regeneration following injury and what accounts for the decreased ability of axon growth over the course of development. Both transient and sustained axon sprouting has been documented in the adult CNS as the anatomical basis of structural plasticity in response to activity deprivation (10). The reason for this reorganization of axons as a compensatory mechanism, in the face of failure to regenerate injured axons, is also unclear. A potential hint to these questions comes from the evolutionarily conserved molecular pathways that control cellular growth and size. It is believed that for most of cell types, specific mechanisms are necessary in preventing cellular overgrowth upon the completion of development (11). Since many of these molecules are often expressed in post-mitotic mature neurons, we hypothesized that these pathways may contribute to the diminished regenerative ability in adult CNS neurons.

By testing different pathways involved in cell growth control in an optic nerve injury model, we show that inhibiting PTEN (phosphatase and tensin homolog), a negative regulator of the mammalian target of rapamycin (mTOR) pathway, in the adult retinal ganglion cells (RGCs) promotes striking axon regeneration. Further studies revealed a two-step suppression of mTOR signaling in adult CNS neurons: first by developmental maturation and second by axotomy-triggered stress response. Such inhibition of mTOR activity and subsequent impairment in new protein synthesis ability contributes to their inability to regenerate injured axons. Reactivating this pathway by inhibiting tuberous sclerosis complex 1 (TSC1), another negative regulator of the mTOR pathway, also leads to extensive long-distance axon regeneration. Our work shows that general growth control pathways regulate axon regenerative abilities in neurons, thereby providing new strategies to promote axon regeneration after CNS injury such as spinal cord injury, stroke, traumatic brain injury and glaucoma.

Subsequent to our priority filing date, Nakashima et al. (J Neurosci (2008 Jul. 16) 28(29):7293-303) reported small-molecule protein tyrosine phosphatase inhibition using potassium bisperoxo(1,10-phenanthroline)oxovanadate (V) as a neuroprotective treatment after spinal cord injury in adult rats.

SUMMARY OF THE INVENTION

The invention provides methods and compositions for promoting survival of, or axon regrowth (regeneration and sprouting) in a lesioned mature central nervous system (CNS) neuron in situ. The general methods comprise: (a) contacting the neuron with a therapeutically effective amount of an exogenous activator of protein translation in the neuron, and thereby promote survival of, or axon regeneration in the neuron; and (b) detecting the resultant promotion of the survival of, or axon regeneration in the neuron.

In particular embodiments, the activator of protein translation is: (a) a mTOR pathway activator; (b) a PTEN inhibitor; (c) a TSC1/2 inhibitor; (d) an Akt activator; (e) a Ras/MEK pathway activator; or (f) a PRAS40 inhibitor.

In particular embodiments, the activator of is a PTEN inhibitor such as (a) potassium bisperoxo(bipyridine)oxovanadate (V) (bpV(bipy)); (b) dipotassium bisperoxo(5-hydroxypyridine-2-carboxyl)oxovanadate (V) (bpV(HOpic)); (c) potassium bisperoxo(1,10-phenanthroline)oxovanadate (V), (bpV(phen)); or (d) dipotassium bisperoxo(picolinato)oxovanadate (V), (bpV(pic)).

In various embodiments, the lesion results from a traumatic injury, traumatic brain injury, a stroke, an acute spinal cord injury, or CNS degeneration.

In specific embodiments, the lesioned axon is in the optic nerve, or is a CNS axon of a sensory neuron, or is in the spinal cord.

In a specific embodiment, the lesioned axon is in the spinal cord of a patient, and the inhibitor is intrathecally administered to the patient.

In various embodiments, the axon is a CNS axon of a sensory neuron, or a CNS axon of a cerebellar granule neuron.

The detecting step may be effected by an indirect or direct assay of axon regeneration.

In various embodiments, the inhibitor is administered intravenously, intrathecally, ocularly, or locally at the neuron.

In a particular embodiment, the general method further comprise an antecedent step of determining that the neuron is lesioned, and has axotomy-induced stress and/or pathology-induced down-regulation of protein translation.

In a particular embodiment, the activator of is a PTEN inhibitor, the lesioned axon is in the optic nerve, and the inhibitor is administered ocularly.

In another aspect, the invention provides compositions specifically adapted to the subject methods, such as a device for promoting survival of, or axon regeneration in a lesioned mature central nervous system (CNS) neuron in situ determined to have axotomy-induced stress and/or pathology-induced down-regulation of protein translation, comprising a reservoir loaded with a premeasured and contained amount of a therapeutically effective amount of an activator of protein translation in the neuron, and specifically adapted for implementing the subject methods.

DETAILED DESCRIPTION OF SPECIFIC EMBODIMENTS OF THE INVENTION

The target neuron is lesioned and has axotomy-induced stress and/or pathology-induced down-regulation of protein translation, which may be detected directly, indirectly, or inferred. In particular examples the lesioned axon is a CNS axon of a dorsal root ganglion (DRG) sensory neuron, a cerebellar granule neuron, or an ocular neuron. The mature (i.e. terminally-differentiated, non-embryonic) neuron may be in vitro or in situ in a subject or patient. In specific embodiments, the subject is a mammal (e.g. human, companion animal, livestock animal, rodent or primate animal model for neurodegeneration or CNS injury, etc.).

The lesion can result from traumatic injury, optic nerve injury or disorder, brain injury, stroke, chronic neurodegeneration such as caused by neurotoxicity or a neurological disease or disorder (e.g. Huntington's disease, Parkinson's disease, Alzheimer's disease, multiple system atrophy (MSA), etc.).

In one embodiment, the activator is used to treat an ocular injury or disorder (e.g. toxic amblyopia, optic atrophy, higher visual pathway lesions, disorders of ocular motility, third cranial nerve palsies, fourth cranial nerve palsies, sixth cranial nerve palsies, internuclear ophthalmoplegia, gaze palsies, eye damage from free radicals, etc.), or an optic neuropathy (e.g. ischemic optic neuropathies, toxic optic neuropathies, ocular ischemic syndrome, optic nerve inflammation, infection of the optic nerve, optic neuritis, optic neuropathy, papilledema, papillitis, retrobulbar neuritis, commotio retinae, glaucoma, macular degeneration, retinitis pigmentosa, retinal detachment, retinal tears or holes, diabetic retinopathy, iatrogenic retinopathy, optic nerve drusen, etc.).

In a particular embodiment, the lesion results from acute or traumatic injury such as caused by contusion, laceration, acute spinal cord injury, etc. In specific embodiments, the lesioned CNS axon is in CNS white matter, particularly white matter that has been subjected to traumatic injury. In certain embodiments, the contacting step is initiated within 96, 72, 48, 24, or 12 hours of formation of the lesion. In various embodiments, the contacting step is initiated, and/or treatment is continued, more than 5, 7, 14, 30, or 60 days after formation of the lesion.

The activator can be administered to the injured neuron in combination with, or prior or subsequent to, other treatments such as the use of anti-inflammatory or anti-scarring agents, growth or trophic factors, etc. In a specific embodiment, the lesion results from acute spinal cord injury and the method additionally comprises contacting the neuron with methylprednisolone sufficient to reduce inflammation of the spinal cord. In various other embodiments, the activator is administered in combination with trophic and/or growth factors such as NT-3 (Piantino et al, Exp Neurol. 2006 October; 201(2): 359-67), inosine (Chen et al, Proc Natl Acad Sci USA. (2002) 99:9031-6; U.S. Pat. No. 6,551,612 to Benowitz; U.S. Pat. No. 6,440,455 to Benowitz; and US Pat Publ 20050277614 to Benowitz), oncomodulin (Yin et al, Nat Neurosci. (2006) 9:843-52; US Pat Publ 20050054558 to Benowitz; US Pat Publ 20050059594 to Benowitz; and U.S. Pat. No. 6,855,690 to Benowitz), etc.

We have documented the suitability in the subject methods and compositions of a wide variety of activators of protein synthesis, and alternative suitable activators are readily identified using the assays described and exemplified herein. In general, the activator increases the effective amount of one or more positive regulators of protein synthesis (such as RheB1, Akt, Ras, etc.), or inhibits the effective amount of one or more negative regulators of protein synthesis (such as PTEN, TSC1, TSC2, PRAS40, etc.). Increasing positive regulators can be effected by simply employing the positive regulator or a more active variant thereof as the activator. Inhibiting negative regulators can be effected at the level of transcription (e.g. using specific siRNA), or by targeting the negative regulator with specific pharmacological inhibitors. Exemplary suitable activators include: mTOR pathway activators, such as active RheB1; PTEN inhibitors, such as established vanadium-based PTEN inhibitors or siRNA; TSC1/2 inhibitors, such as siRNA for TSC2 or TSC1; Akt activators, such as active Akt and menadione; Ras/MEK pathway activators, such as active Ras; and PRAS40 inhibitors, such as siRNA. Alternative, suitable activators of protein synthesis are readily identified, confirmed and characterized using the assays and protocols disclosed herein.

In particular embodiments, the activator is a PTEN inhibitor, particularly a vanadium-based PTEN inhibitor, such as sold commercially by Calbiochem, EMD/Merck, including (a) potassium bisperoxo(bipyridine)oxovanadate (V) (bpV (bipy)); (b) dipotassium bisperoxo(5-hydroxypyridine-2-carboxyl)oxovanadate (V) (bpV(HOpic)); (c) potassium bisperoxo(1,10-phenanthroline)oxovanadate (V), (bpV(phen)); and (d) dipotassium bisperoxo(picolinato)oxovanadate (V), (bpV(pic)). Alternative, suitable PTEN inhibitors include PTEN inhibitor compounds of formulas I-XIV as described in WO2005/097119; vanadium-based PTEN inhibitors described in US20070292532 and by Rosivatz et al. 2006 (ACS Chem. Biol. 1(12) 780-790); the 1,4-naphthoquinone derivative, shikonin, described by Nigorikawa et al. (Mol Pharmacol 70:1143-1149, 2006); and menadione (vitamin K3) as described by Yoshikawa et al., Biochim Biophys Acta.

2007 April; 1770(4):687-93. PTEN inhibition assays for general screening (to identify and confirm alternative, suitable inhibitors) and IC50 determinations are known in the art, e.g. WO 2005/097119; see also Example 2, below.

Suitable PTEN inhibitors are also described in WO 2007/0203098, including all recited genera, subgenera and species disclosed and as described therein including:

I) Ascorbic Acid-Based PTEN Inhibitors

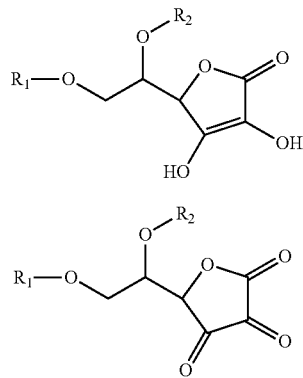

Formula I

Formula Ia wherein,
R1 represents H, C1-C3 alkyl, aryl, alkylaryl, $(CH_2)_n$COXR3, $(CH_2)_n$XCOR3, $(CH_2)_n$COR3, $(CH_2)_n$SO$_2$R3, $(CH_2)_n$XR3, $(CH_2)_n$SO$_2$X—R3, $(CH_2)_n$XSO$_2$R3, $(CH_2)_n$NR3R4, or $(CH_2)_n$CO$(CH_2)_m$XR3;
R2 represents H, C1-C3 alkyl, aryl, alkylaryl, $(CH_2)_n$COX—R3, $(CH_2)_n$XCOR3, $(CH_2)_n$COR3, $(CH_2)_n$SO$_2$R3, $(CH_2)_n$XR3, $(CH_2)_n$SO$_2$X—R3, $(CH_2)_n$XSO$_2$R3, $(CH_2)_n$NR3R4, or $(CH_2)_n$CO$(CH_2)_m$XR3;
R3, R5 and R6 independently are H, C1-C4 alkyl, aryl or alkylaryl;
R4 represents H, C1-C4 alkyl, aryl, alkylaryl, NHSO$_2$R5, NHCO$_2$R5, or NR5R6;
m=0 to 3;
n=0 to 3; and
X represents O or NR4.
Compounds of Formula I and Ia may have ester linkages at either R1 or R2.

II) 1,2,3-triazole PTEN Inhibitors (Such as Described in WO02/32896)

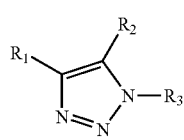

Formula II wherein,
R1 represents H, C1-C4 alkyl, aryl, alkylaryl, COXR2, COR2, SO$_2$XR2, SO$_2$R2;
R2 represents H, C1-C4 alkyl, aryl, alkylaryl, $(CH_2)_n$COXR4, $(CH_2)_n$XCOR4, $(CH_2)_n$X R4, $(CH_2)_n$SO$_2$XR4, $(CH_2)_n$XSO$_2$R4, NHSO$_2$R4, NHCOR4, NHCO$_2$R4, NHCOCO$_2$R4, or NR4R5;
R3 represents H, C1-C4 alkyl, aryl, alkylaryl, $(CH_2)_n$COXR4, $(CH_2)_n$XCOR4, $(CH_2)_n$X R4, $(CH_2)_n$SO$_2$XR4, $(CH_2)_n$XSO$_2$R4, NHSO$_2$R4, NHCOR4, NHCO$_2$R4, NHCOCO$_2$R4, or NR4R5;
R4 represents H, C1-C4 alkyl, aryl, or alkylaryl;
R5 represents H, C1-C4 alkyl, aryl, alkylaryl, NHSO$_2$R6, NHCOR6, NHCO$_2$R6, NR6R7, or N=C(R6R7);
R6 represents H, C1-C4 alkyl, aryl, or alkylaryl;
R7 represents H, C1-C4 alkyl, aryl, or alkylaryl;
n=0-3; and
X represents O or NRS.
The inhibitors of Formula II include:

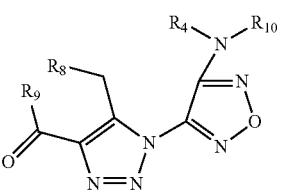

Formula IIa wherein,
R8 represents $(CH_2)_n$XR4, or $(CH_2)_n$SR4;
R9 represents NHNHSO$_2$aryl, NHNHCO-aryl, or NHN=C(R6R7); and
R10 represents H, C1-C4 alkyl, aryl, alkylaryl, SO$_2$R6, CORE, or CO$_2$R6.

III) Diamide PTEN Inhibitors

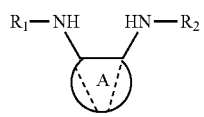

Formula III wherein,
A is a five or six member ring;
R1 represents H, C1-C3 alkyl, aryl, alkylaryl, $(CH_2)_n$COXR3, $(CH_2)_n$XCOR3, $(CH_2)_n$COR3, $(CH_2)_n$SO$_2$R3, $(CH_2)_n$XR3, $(CH_2)_n$SO$_2$XR3, $(CH_2)_n$XSO$_2$R3, NHSO$_2$R3, NHCO$_2$R3, NHCOR3, NHCO$_2$R3, NHCOCO$_2$R3, NR3R4, or $(CH_2)_n$CO$(CH_2)_m$XR3;
R2 represents H, C1-C3 alkyl, aryl, alkylaryl, $(CH_2)_n$COXR3, $(CH_2)_n$XCOR3, $(CH_2)_n$COR3, $(CH_2)_n$SO$_2$R3, $(CH_2)_n$XR3, $(CH_2)_n$SO$_2$XR3, $(CH_2)_n$XSO$_2$R3; NHSO$_2$R3, NHCO$_2$R3, NHCOR3, NHCO$_2$R3, NHCOCO$_2$R3, NR3R4, or (CH2)nCO$(CH_2)_m$XR3;
R3 represents H, C1-C4 alkyl, aryl, or alkylaryl;
R4 represents H, C1-C4 alkyl, aryl, alkylaryl, NHSO$_2$R5, NHCO$_2$R5, or NR5R6;
R5 represents H, C1-C4 alkyl, aryl, or alkylaryl;
R6 represents H, C1-C4 alkyl, aryl, or alkylaryl;
n=0-3;
m=0-3; and
X represents O, or NR4.

Ring A may be saturated, unsaturated, or aromatic, and may optionally comprise N and O. Preferred compounds of formula III are those wherein ring A is selected from heterocyclic ring systems, especially vicinally substituted pyridines, pyrimidines, furazans, imidazoles, pyrrazoles, furaus, thiazoles, and oxazoles, as well as their saturated analogs; other preferred inhibitors of formula III are those wherein ring A comprises an all carbon aromatic rings, such as substituted and unsubstituted phenyl, and their saturated analogs.

The inhibitors of Formula III may comprise a ring A selected from the following:

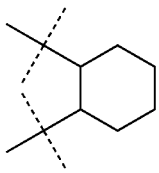

Formula IIIA

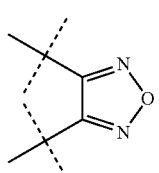

Formula IIIB

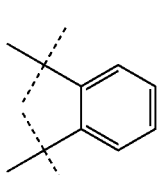

Formula IIIC

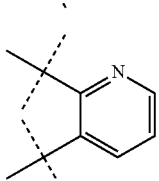

Formula IIID

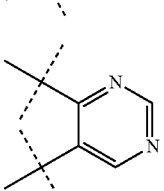

Formula IIIE

The inhibitors of Formula III comprising a ring A selected from IIIA, IIIB, IIIC, IIID, IIIE may further comprise:

R1 represents H, C1-C3 alkyl, aryl, alkylaryl, $(CH_2)_nCOR3$, or $(CH_2)_nSO_2R3$;

R3 represents H, C1-C4 alkyl, aryl, or alkylaryl;

R7 represents H, C1-C4 alkyl, halogens, $NO_2$, $CF_3$, aryl, carboxylate, aryloxy, amino, alkylamino, cyano, isocyanate, alkoxycarbonyl, or haloalkyl;

R8 represents H, C1-C4 alkyl, halogens, $NO_2$, $CF_3$, aryl, carboxylate, aryloxy, amino, alkylamino, cyano, isocyanate, alkoxycarbonyl, or haloalkyl; and m=1, 2, 3.

In particular embodiments, alkylaryl is selected from Formula IIIF or IIIG:

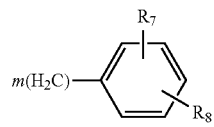

Formula IIIF

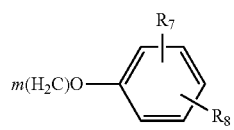

Formula IIIG

The inhibitors of Formula III may also be of the formula:

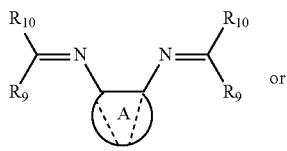

Formula IIIH or

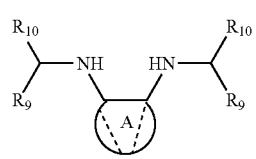

Formula IIIJ wherein,

A is a five or six member ring;

R9 represents H, C1-C3 alkyl, aryl, alkylaryl, $(CH_2)_n COXR3$, $(CH_2)_n XCOR3$, $(CH_2)_n COR3$, $CH_2(CH_2)_n SO_2R3$, $CH_2(CH_2)_n XR3$, $CH_2(CH_2)_n SO_2XR3$, or $CH_2(CH_2)_n XSO_2R3$;

R10 represents H, C1-C3 alkyl, aryl, alkylaryl, $(CH_2)_n COXR3$, $(CH_2)_n XCOR3$, $(CH_2)_n COR3$, $CH_2(CH_2)_n SO_2R3$, $CH_2(CH_2)nXR3$, $CH_2(CH_2)_n SO_2XR3$, or $CH_2(CH_2)_n XSO_2R3$; and R3, X, and n are as described for Formula III.

Ring A of inhibitors IIIH and IIIJ may be saturated, unsaturated or aromatic, and may optional be substituted with C and N.

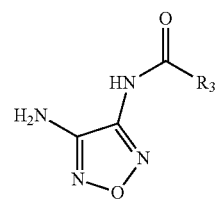

Compound 3-1

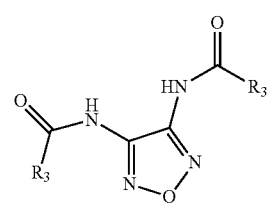

Compound 3-2

-continued

Compound 3-3
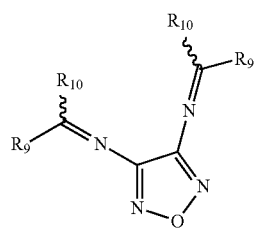

Compound 3-4
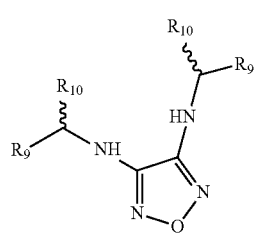

IV) Aryl imidazole Carbonyl PTEN Inhibitors

Formula IV
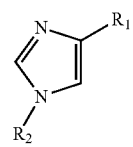

wherein,

R1 represents H, C1-C4 alkyl, aryl, alkylaryl, (CH₂)nCOXR3, (CH₂)$_m$XCOR3, (CH₂)$_m$XR3, (CH₂)$_n$COR3, (CH₂)$_n$SO₂XR3, or (CH₂)$_m$XSO₂R3;

R2 represents H, C1-C4 alkyl, aryl, or alkylaryl;

R3 represents H, C1-C3 alkyl, aryl, or alkylaryl;

R4 represents H, C1-C4 alkyl, aryl, alkylaryl, NHSO₂R5, NHCO₂R5, N=C(R5R6), or NR5R6;

R5 represents H, C1-C4 alkyl, aryl, or alkylaryl;

R6 represents H, C1-C4 alkyl, aryl, or alkylaryl;

m=1-3;

n=0-3; and

X represents O, NR4.

Compounds of formula IV may be of the formula:

Formula IVA
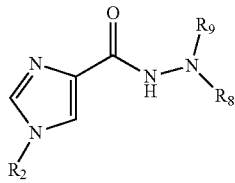

wherein, R7 represents XR4.

Compounds of formula IV may also be of the formula:

Formula IVB
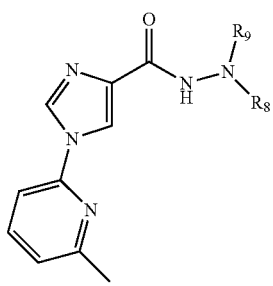

wherein

R8 represents H, C1-C4 alkyl, aryl, alkylaryl, (CH₂)$_n$COX—R3, (CH₂)$_n$XCOR3, (CH2)nX—R3, (CH₂)$_n$COR3, (CH₂)$_n$SO₂XR3, or (CH₂)$_n$XSO₂R3; and R9 represents H, C1-C4 alkyl, aryl, alkylaryl.

Compounds of Formula IVB may also be selected:

Formula IVC
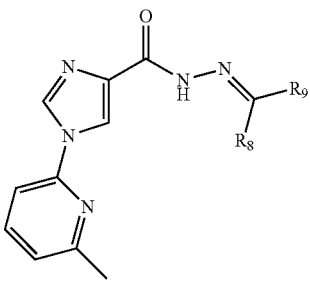

Formula IVD

Compound 4-1
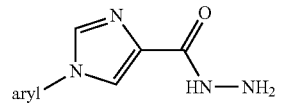

Compound 4-2
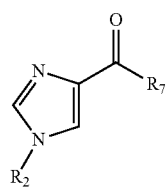

Compound 4-3
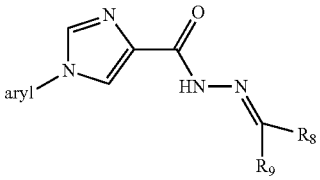

V) Polyamide PTEN inhibitors

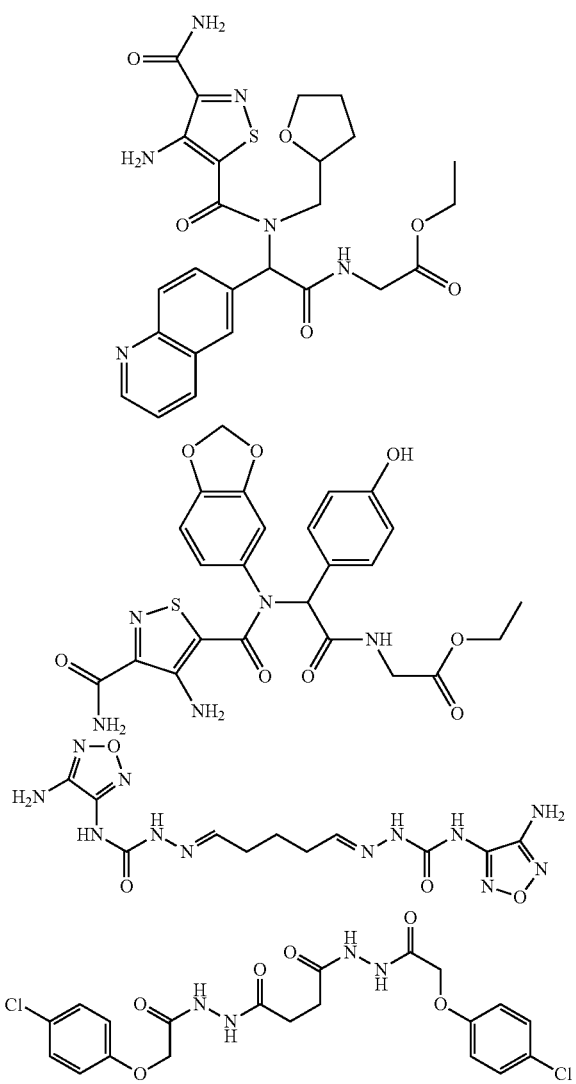

VI) Commercial PTEN inhibitors
1. Deltamethrin; (S)-a-Cyano-3phenoxybenzyl(1R)-cis-3-(2,2 dibromovinyl)-2,2-dimethylcyclopropanecarboxylate
2. Alendronate, Sodium, Trihydrate
3. N-(9,10-Dioxo9,10-dihydrophenanthren-2-yl)-2,2-dimethylpropionamide
4. 5-Benzyl-3furylmethyl (1R,S)-cis,trans-chrysanthemate
5. Suramin, Sodium Salt; 8,8'-[carbonylbis[imino-3,1phenylenecarbonylimino (4-methyl-3,1-phenylene)carbonylimino]]bis-, hexasodium salt
6. 4-Methoxyphenacyl Bromide
7. 1,4-Dimethylendothall; 1,4-Dimethyl-7-oxabicyclo[2.2.1]heptane-2,3-dicarboxylic Acid
8. Cantharidic Acid; 2,3-dimethyl-7-oxabicyclo[2.2.1]heptane-2,3dicarboxylic acid
9. Sodium Stibogluconate; Antimony Sodium Gluconate
10. 3,4-Dephostatin, Ethyl-
11. Fenvalerate; a-Cyano-3-phenoxybenzyl-a(4-chlorophenyl)isovalerate
12. α-Naphthyl Acid Phosphate, Monosodium Salt
13. β-Glycerophosphate, Disodium Salt, Pentahydrate
14. Endothall; 7-Oxabicyclo[2.2.1]heptane-2,3dicarboxylic Acid
15. Cypermethrin; (R,S)-α-Cyano-3-phenoxybenzyl-3(2,2-dichlorovinyl)-2,2-dimethylcyclopropanecarboxylate; (1R)—(R)cyano(3-phenoxyphenyl) methyl 3-(2,2-dichlorovinyl)-2,2dimethylcyclopropanecarboxylate.

VII) 1,10-phenanthroline-5,6-dione PTEN Inhibitors

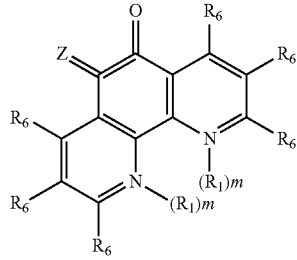

Formula VII wherein,
R1 represents 0, C1-C4 alkyl, $(CH_2)_n COXR2$, $(CH_2)_n X$-$COR2$, $(CH_2)_n XR2$, $(CH_2)_n COR2$, $(CH_2)_n SO_2 XR2$, $(CH_2)_n XSO_2 R2$, or $(CH_2)nSO_2 R2$;
R2 represents H, C1-C4 alkyl, aryl, alkylaryl, $NHSO_2 R4$, $NHCOR4$, $NHCO_2 R4$, $NHCOCO_2 R4$, or $NR4R5$;
R3 represents H, C1-C4 alkyl, aryl, alkylaryl, $NHSO_2 R4$, $NHCOR4$, $NHCO_2 R4$, $NHCOCO_2 R4$, or $NR4R5$;
R4 represents H, C1-C4 alkyl, aryl, or alkylaryl;
R5 represents H, C1-C4 alkyl, aryl, or alkylaryl;
R6 at each occurrence is independently selected from hydrogen, halogen, $NO_2$, $NR4R10$, C1-C4 alkyl, $NH(CH_2)_p CO$ $(CH_2)_q XR2$, $(CH_2)_p COXR2$, $(CH_2)_p XCOR2$, $(CH_2)_p XR2$, $(CH_2)pCOR2$, $(CH_2)_p SO_2 XR2$, or $(CH_2)_p XSO_2 R2$;
R7 represents H, C1-C4 alkyl, aryl, alkylaryl, $SO_2 R4$, $NHSO_2 R4$, $NHCO_2 R4$, or $NR8R9$;
R8 represents independently H, C1-C4 alkyl, aryl, alkylaryl, $(CH_2)_n COXR2$, or $(CH_2)_n XR2$;
R9 represents independently H, C1-C4 alkyl, aryl, alkylaryl, $(CH_2)nCOXR2$, $(CH_2)_n XR2$, $(CH_2)_p COXR2$, $(CH_2)pX$-$COR2$, $(CH_2)~R2$, $(CH_2)pCOR2$, $(CH_2)pSO_2 XR2$, $(CH_2)_p XSO_2 R$, or $(CH_2)pSO_2 R2$;
R10 represents H, C1-C4 alkyl R7=H, C1-C4 alkyl, aryl, alkylaryl, $SO_2 R4$, $NHSO_2 R4$, $NHCO_2 R4$, or $NR8R9$;
m represents independently 0 or 1;
n=1-5;
p=0-5;
q=0-5;
X represents 0 or NR3; and
Z=O or NR7.

The nitrogen in the ring of compound of Formula VII may be neutral. The nitrogen may also be charged when bound to an R1 group (quaternary salt) in the case where at least one m=1.
The inhibitor may also be selected from:

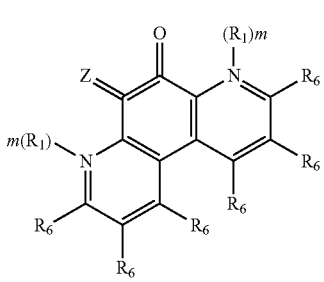

Formula VIIA

-continued

Formula VIIB
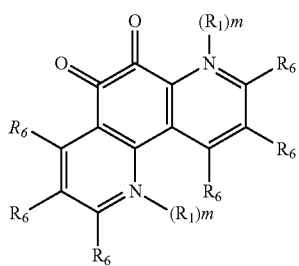

Formula VIIC
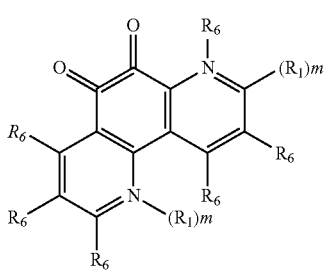

Compound 7-3
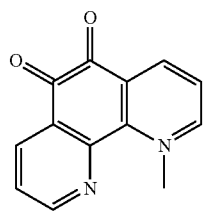

Compound 7-5
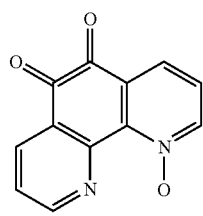

Compound 7-8
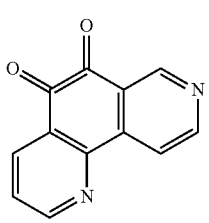

Compound 7-10
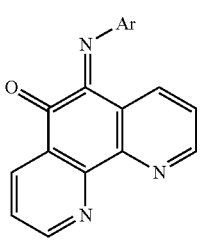

VIII) Substituted Phenathrene-9-10-dione PTEN Inhibitors

Formula VIII
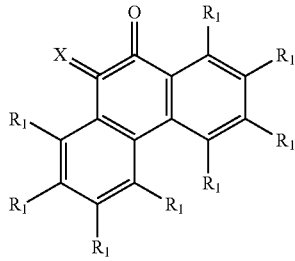

wherein,

R1 represents H, NO$_2$, NR5R6, halogen, cyano, alkyl, alkylaryl, carbonyl, carboxy, COR2, or CONR5R6;

R2 and R3 represent independently H, C1-C4 alkyl, aryl, or alkylaryl;

R4 represents H, C1-C4 alkyl, aryl, alkylaryl, SO$_2$—R2, NHSO$_2$R2, NHCOR2, NHCO$_2$R2, N=CR2R3, or NR5R6;

R5 represents H, C1-C4 alkyl, aryl, alkylaryl, (CH$_2$)$_n$COXR2, (CH$_2$)$_n$XR2, CH$_2$)$_n$CO(CH$_2$)$_m$XR2, SO$_2$R2, (CH2)nCO(CH2)nCOXR2, or (CH$_2$)$_n$COR2;

R6 represents H, C1-C4 alkyl, aryl, alkylaryl, (CH$_2$)$_n$COX—R2, (CH$_2$)$_n$XR2, (CH$_2$)$_n$CO(CH$_2$)$_m$XR2, SO$_2$R2, (CH$_2$)$_n$CO(CH$_2$)$_n$COXR2, or (CH$_2$)$_n$COR2;

m=0-3;

n=0-3; and

X represents CR2R3, O, NR4.

The inhibitors of Formula VIII may be of the formula:

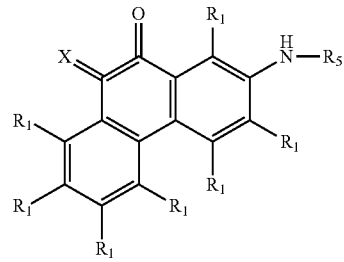

Compound 8-3
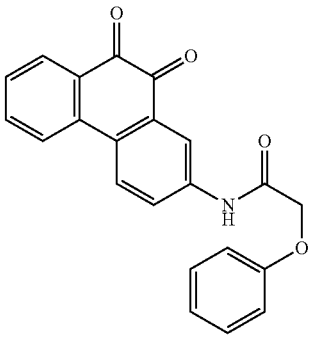

-continued

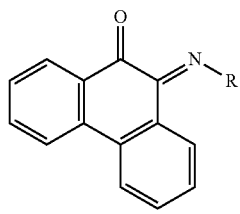

Compound 8-4

IX) Isatin PTEN Inhibitors

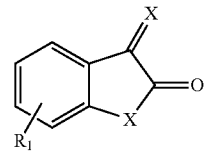

Formula IX wherein,

R1 represents H, NO$_2$, NR5R6, halogen, cyano, alkyl, alkylaryl, carbonyl, carboxy, COR$_2$, CONR5R6, SO$_3$R2, or SO$_2$NR2R3;

R2 and R3 represent independently H, C1-C4 alkyl, aryl, or alkylaryl;

R4 represents H, C1-C4 alkyl, aryl, alkylaryl, SO$_2$—R2, NHSO$_2$R2, NHCOR2, NHCO$_2$R2, N=CR2R3, or NR5R6;

R5 represents H, C1-C4 alkyl, aryl, alkylaryl, (CH$_2$)$_n$COX—R$_2$, (CH$_2$)$_n$X—R$_2$, (CH$_2$)$_n$CO(CH$_2$)$_m$XR2, SO$_2$R2, (CH$_2$)$_n$CO(CH$_2$)$_n$COXR2, or (CH$_2$)$_n$COR2;

R6 represents H, C1-C4 alkyl, aryl, alkylaryl, (CH$_2$)$_n$COX—R2, (CH$_2$)$_n$X—R2 (CH$_2$)$_n$CO(CH$_2$)=XR2, SO$_2$R2, (CH$_2$)$_n$CO(CH$_2$)$_n$COXR2, or (CH$_2$)$_n$COR2;

m=0-3;

n=0-3; and

X represents CR2R3, O, NR4.

The inhibitors of Formula IX may be selected from:

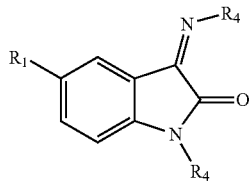

Formula IXA

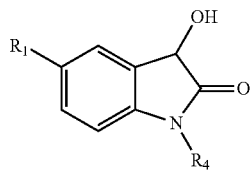

Formula IXB

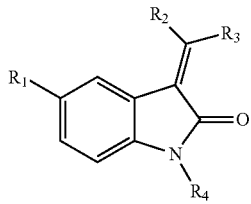

Formula IXC

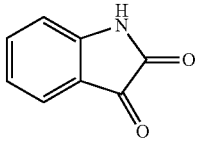

Structure 9-1

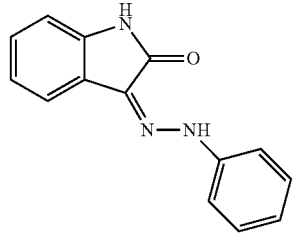

Structure 9-2

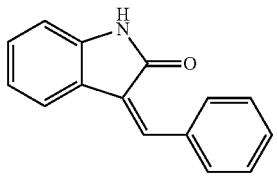

Structure 9-4

X) Substituted Phenanthren-9-ol PTEN Inhibitors

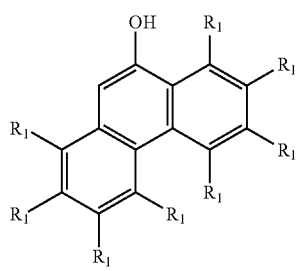

Formula X

R1 represents H, N02, NR5R6, halogen, cyano, alkyl, alkylaryl, carbonyl, carboxy, COR2, or CONR5R6;

R2 and R3 represent independently H, C1-C4 alkyl, aryl, or alkylaryl;

R4 represents H, C1-C4 alkyl, aryl, alkylaryl, SO$_2$—R2, NHSO$_2$R2, NHCOR2, NHCO$_2$R2, N=CR2R3, or NR5R6;

R5 represents H, C1-C4 alkyl, aryl, alkylaryl, (CH$_2$)$_n$COXR2, (CH$_2$)$_n$X—R2, (CH$_2$)$_n$CO(CH$_2$)$_m$XR2, SO$_2$R2, (CH$_2$)$_n$CO(CH$_2$)$_n$COXR2, or (CH$_2$)$_n$COR2;

RO represents H, C1-C4 alkyl, aryl, alkylaryl, (CH$_2$)$_n$COX—R2, CCH$_2$)$_n$X—R2, (CH$_2$)$_n$CO(CH$_2$)$_m$XR2, SO$_2$R2, (CH$_2$)$_n$CO(CH$_2$)$_n$COXR2, (CH$_2$)$_n$COR2;

m=0-3;

n=0-3; and

X represents CR2R3, O, NR4.

Compound 10-3

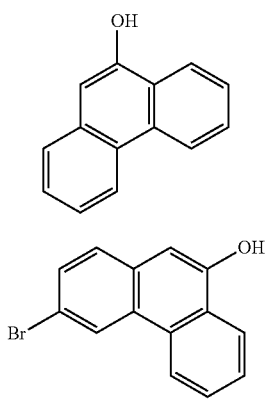

Compound 10-4

XI) Substituted Naphthalene-1,2-dione PTEN Inhibitors

Formula XI

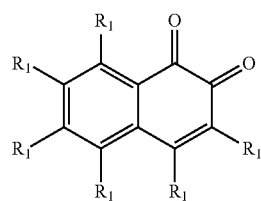

wherein,

R1 represents independently chosen from H, NO$_2$, NR3R4, halogen, cyano, alkyl, alkylaryl, carbonyl, carboxy, (CH$_2$)$_n$COXR3, COR2, SO$_3$—R2, SO$_2$N—R3R4, NHSO$_2$—R3, NHCO$_2$R3, NHCOR3, NHCOCO$_2$R2, NR3R4, or CONR3R4;

R2 represents H, C1-C4 alkyl, aryl, or alkylaryl;

R3 and R4 represent independently H, C1-C4 alkyl, aryl, alkylaryl, (CH$_2$)$_n$COXR2, (CH$_2$)$_n$CO(CH$_2$)$_m$XR2, or (CH$_2$)$_n$OR2;

m=0-3;

n=0-3; and

X represents O, NR2.

The inhibitors of Formula XI may be selected from:

Formula XIA

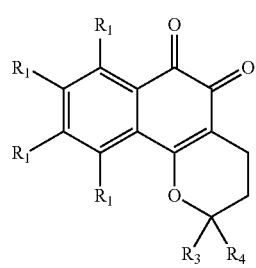

Formula XIB (structure shown)

Compound 11

(structure shown)

Compound 11-1

(structure shown)

XII) Substituted Naphthalene-1,4-dione PTEN Inhibitors

Formula XII

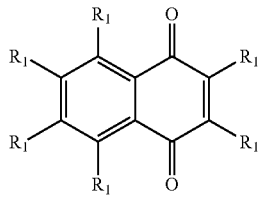

wherein

R1 represents H, NO$_2$, NR3R4, halogen, cyano, alkyl, alkylaryl, carbonyl, carboxy, (CH$_2$)nCOXR3, COR2, SO$_3$R2, SO$_2$N—R3R4, NHSO$_2$—R3, NHCO$_2$R3, NHCOR3, NHCOCO$_2$R2, NR3R4, or CON—R3R4;

R2 represents H, C1-C4 alkyl, aryl, or alkylaryl;

R3 and R4 represents independently H, C1-C4 alkyl, aryl, alkylaryl, (CH$_2$)$_n$COXR2, (CH$_2$)nCO(CH$_2$)$_m$XR2, or (CH$_2$)$_n$OR2;

m=0-3;

n=0-3; and

X represents O, NR2.

XIII) Vanadate-Based PTEN Inhibitors

1. Potassium Bisperoxo(bipyridine)oxovanadate (V)
2. Dipotassium Bisperoxo(5-hydroxypyridine-2carboxyl)oxovanadate (V)
3. Dipotassium Bisperoxo(picolinato)oxovanadate (V)
4. Monoperoxo(picolinato)oxovanadate (V)
5. Potassiun Bisperoxo(1,10-phenanthroline)oxovanadate (V)
6. bis(N,N-Dimethylhydroxamido)hydroxooxovanadate

XIV) T1-Loop Binding Element Containing PTEN Inhibitors

The PTEN inhibitors may contain a group that exists at physiological pH in significantly anionic form, such as at least 5% of the molecular species at pH of 7.4 are anionic charged. Such anionic groups can bind to PTEN in the T1 loop of the peptide structure in solution.

Representative examples of such groups include:

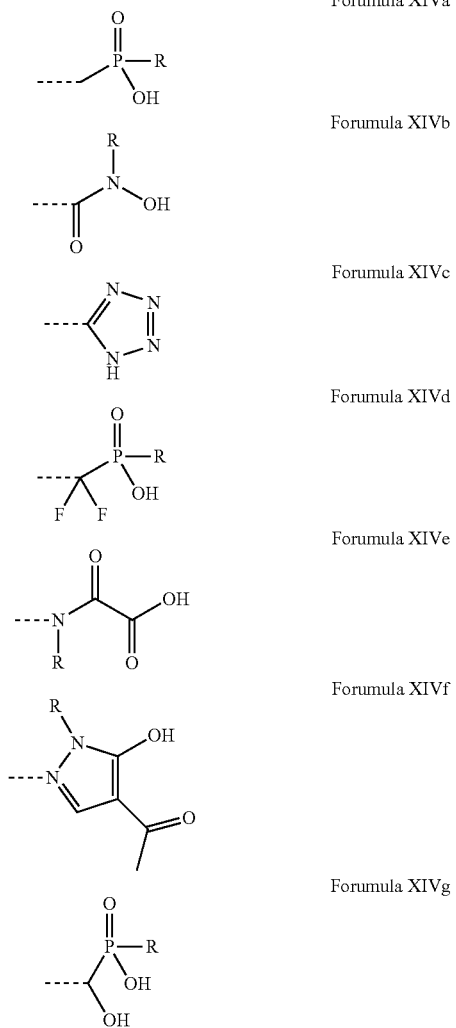

wherein, R is independently chosen from H, OH, O-alkyl, alkyl, SH, S-alkyl, NH2, NH-alkyl, N-(alkyl)2 where alkyl is a small, C1-C4 alkyl moiety. The dashed lines represent the connection to the formulas of the compounds described for Formulas I through XIII above. The groups may be further evaluated in silico for their ability to fill the T1 loop space by standard molecular docking procedures. Such T1-loop binding groups may be incorporated into compounds of Formula I-XIII. Incorporation of the groups may impart selectivity of the molecules to inhibition of PTEN. Preparation of groups XIVa-XIVd are well established in the literature. Compounds of Formula XIVe may be prepared by methods disclosed in Wilson et al., Bioorganic & Medicinal Chemistry Letters, vol 6, No. 9, pp 1043-1046, 1996. Incorporation of these groups into the Formulas I-XIII is by standard synthetic methods easily attainable by those skilled in the art. Examples of such incorporation by simply utilizing appropriate starting materials is illustrated by the conversion of 7-9 to one incorporating the above groups, e.g.:

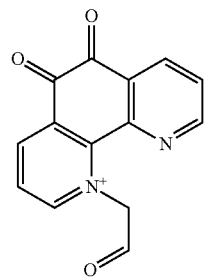

Compound 14-1

The activator is contacted with the neuron using a suitable drug delivery method and treatment protocol sufficient to promote regeneration of the axon. For in vitro methods, the activator is added to the culture medium, usually at nanomolar or micromolar concentrations. For in situ applications, the activator can be administered orally, by intravenous (i.v.) bolus, by i.v. infusion, subcutaneously, intramuscularly, ocularly (intraocularly, periocularly, retrobulbarly, intravitreally, subconjunctivally, topically, by subtenon administration, etc.), intracranially, intraperitoneally, intraventricularly, intrathecally, by epidural, etc.

Depending on the intended route of delivery, the compositions may be administered in one or more dosage form(s) (e.g. liquid, ointment, solution, suspension, emulsion, tablet, capsule, caplet, lozenge, powder, granules, cachets, douche, suppository, cream, mist, eye drops, gel, inhalant, patch, implant, injectable, infusion, etc.). The dosage forms may include a variety of other ingredients, including binders, solvents, bulking agents, plasticizers etc.

In a specific embodiment, the activator is contacted with the neuron using an implantable device that contains the activator and that is specifically adapted for delivery to a CNS axon of neuron. Examples of devices include solid or semi-solid devices such as controlled release biodegradable matrices, fibers, pumps, stents, adsorbable gelatin (e.g. GEL-FOAM®), etc. The device may be loaded with premeasured, discrete and contained amounts of the activator sufficient to promote regeneration of the axon. In a particular embodiment, the device provides continuous contact of the neuron with the activator at nanomolar or micromolar concentrations, preferably for at least 2, 5, or 10 days.

The subject methods typically comprise the further step of detecting a resultant regeneration of the axon. For in vitro applications, axonal regeneration may be detected by any routinely used method to assay axon regeneration such as a neurite outgrowth assay. For in situ applications, axonal regeneration can be detected directly using imaging methodologies such as MRI, or indirectly or inferentially, such as by neurological examination showing improvement in the targeted neural function. The detecting step may occur at any time point after initiation of the treatment, e.g. at least one day, one week, one month, three months, six months, etc. after initiation of treatment. In certain embodiments, the detecting step will comprise an initial neurological examination and a subsequent neurological examination conducted at least one day, week, or month after the initial exam. Improved neurological function at the subsequent exam compared to the initial exam indicates resultant axonal regeneration. The specific detection and/or examination methods used will usually be based on the prevailing standard of medical care for the particular type of axonal lesion being evaluated (i.e. trauma, neurodegeneration, etc.).

The invention also provides activator-eluting or activator-impregnated CNS implantable solid or semi-solid devices. Examples of CNS implantable devices include polymeric microspheres (e.g. see Benny et al., Clin Cancer Res. (2005) 11:768-76) or wafers (e.g. see Tan et al., J Pharm Sci. (2003) 4:773-89), biosynthetic implants used in tissue regeneration after spinal cord injury (reviewed by Novikova et al., Curr Opin Neurol. (2003) 6:711-5), biodegradable matrices (see e.g. Dumens et al., Neuroscience (2004) 125:591-604), biodegradable fibers (see e.g. U.S. Pat. No. 6,596,296), osmotic pumps, stents, adsorbable gelatins (see e.g. Doudet et al., Exp Neurol. (2004) 189:361-8), etc. Preferred devices are particularly tailored, adapted, designed or designated for CNS implantation. The implantable device may contain one or more additional agents used to promote or facilitate neural regeneration. For example, in one embodiment, an implantable device used for treatment of acute spinal cord injury contains the activator and methylprednisolone or other anti-inflammatory agents. In another embodiment, the implantable device contains the activator and a nerve growth factor, trophic factor, or hormone that promotes neural cell survival, growth, and/or differentiation, such as brain-derived neurotrophic factor (BDNF), ciliary neurotrophic factor (CNTF), nerve growth factor (NGF), inosine, oncomodulin, NT-3, etc.

EXAMPLE 1

Promoting Axon Regeneration in the Mature CNS by Promoting Protein Translation

Germline knockout of individual cell growth control genes result in either embryonic lethality or have compromised viability in mice, thus limiting the utility of these animals in adult axon regeneration studies. To circumvent this problem, we utilized a viral strategy to express Cre recombinase to conditionally delete specific genes in adult RGCs. To validate efficient expression of Cre in RGCs, we injected adeno-associated viruses expressing Cre (AAV-Cre) into the vitreous body of the eye in reporter mice (Rosa-STOP-PLAP) in which PLAP ((human placenta alkaline phosphatase) activity is dependent on the expression of Cre. We found that PLAP expression is induced in more than 90% of RGCs, indicating that AAV-Cre is highly efficient in infecting RGCs in adult mice. The completeness of optic nerve transection was verified by the observations that after lesion both retrograde and anterograde tracers fail to reach the retina or the superior colliculi (SC), respectively. Because lens injury and subsequent activation of macrophages have been reported to promote axon regeneration in vivo (9), the micropipette used for injections was angled in such a way to avoid touching lens. We verified that this method resulted in no significant macrophage/microglia activation after intravitreal AAV injection as indicated by anti-CD68 antibody staining.

To test the effects of conditional deletion of growth control molecules on axon regeneration in adult RGCs, we injected AAV-Cre into the vitreous body of different adult floxed mice, including Rbf/f (12), P53f/f (12), Smad4f/f (13), Dicerf/f (14), LKB1f/f (15), and PTENf/f (16). The deletion of individual genes in RGCs was verified by in situ hybridization experiments. A standard optic nerve crush assay (9, 17) was therefore performed at 2 weeks following AAV injection. Axon regeneration was assayed by examining axonal fibers labeled with the anterograde tracer, cholera toxin B (CTB), in the optic nerve sections across the lesion site. Since approximately 80% of axotomized RGCs in wild type mice undergo cell death within 2 weeks post-injury (18); neuronal survival was also examined by whole-mount staining of the retina with anti-TUJ1 antibodies (a marker of RGCs).

We found that inhibiting negative regulators of growth promoting pathways promotes neuron survival and/or axon regeneration. PTEN inhibition had the most dramatic effects on both neuronal survival and axon regeneration. In all PTENf/f conditional mutants injected with AAV-Cre, but not with control AAV-GFP, RGCs displayed a significant increase in RGC survival. In addition, striking long-distance axon regeneration was observed at 14 days post-injury. We repeated the AAV-Cre experiments in a second set of PTENf/f mice, as well as AAV-GFP injection as controls, and observed similar results. These data indicate that inhibition of PTEN is sufficient in enhancing regeneration of the injured adult CNS. Quantitatively, an estimated 45% of PTEN-deleted RGCs survived at two weeks post injury, in comparison to approximately 20% in control animals. Of the surviving RGCs, at 2 weeks post-injury, approximately 8-10% regenerate their lesioned axons up to 0.5 mm distal to the lesion epicenter. To our knowledge, this is the first description of such long distance regeneration in the injured adult mammalian optic nerve. Importantly, these regenerating fibers continued to project along the optic nerve over time. At 4 weeks post-injury, some regenerating fibers extended to the area of the optic chiasm. Among the other mouse lines tested, p53-deleted RGCs showed a significant increase in neuronal viability (about 54% of injured RGCs survived) but there was no evidence of axon regeneration in these mice. Since both P53 and PTEN deletion enhanced cell survival, while only PTEN-deletion promoted axon regeneration, these data indicate that inducing neuron survival may not be sufficient to trigger axon regrowth (19). Our results indicate that PTEN-inhibition acts upon intrinsic regenerative mechanisms to promote growth in the adult CNS following injury.

We hypothesized that PTEN-inhibited CNS axons may quickly resume axon elongation after injury. We thus performed intravitreal CTB injection immediately after optic nerve crush to trace axons at early time points post-injury. At the lesion site, an obvious glial response occurred at 1 to 3 days after crushing as indicated by the up-regulation of chondroitin sulfate proteoglycans (CSPGs) expression. Consistent with previous studies (20), GFAP-positive astrocytes are largely excluded from the lesion sites and CSPG signals returned to low levels at 7 days post-injury. At 1 day post-lesion, injured optic nerve fibers terminate at the proximal end of the crush site both in control and in AAV-Cre injected PTENf/f mice. However, at 3 days post-injury, axonal sprouts from PTEN-deficient RGCs started to penetrate into the CSPG-enriched lesion site together with macrophages and some fibers could be seen beyond the lesion sites at 7 days after injury. In contrast, minimum axonal sprouts were seen in control animals at these stages. Electron microscopic analysis confirmed that in the wild type situation, degenerating RGC axons, myelin debris and macrophages occupied injury sites, and few regenerating fibers were visible. However, when PTEN was inhibited in RGCs, regenerative axonal sprouts, often appearing as bundles, were found both within and distal to the lesion site in early days post-injury. These results indicated that PTEN-inhibition indeed enabled axons to overcome inhibition in the lesion site and to regenerate soon after injury.

PTEN deletion is known to result in the activation of PI3K/mTOR pathway, which is critical in controlling cell growth and size by regulating the cap-dependent protein translation initiation (21-24). Because axon regeneration requires substantial new protein synthesis, we hypothesized that mTOR activation could underlie axon regrowth in PTEN-deleted neurons. PTEN and different forms of PI3 kinases are expressed in wild type adult RGCs. Two of the well-studied targets of the mTOR kinase that mediates its effects on protein translation are ribosomal S6 kinase 1 (S6K1) and the eukaryotic initiation factor 4 E (eIF4E)-binding protein 4E-BP1. Phospho-S6K1 in turn phosphorylates ribosomal protein S6. Previous studies have used the phosphorylation of S6 and 4E-BP1 as indicators of mTOR activation (25, 26). Phosphorylated-S6 (p-S6) staining revealed a dramatic development-dependent decline in the percentage of p-S6 positive RGCs. Strong p-S6 signals can be seen in most embryonic neurons, but remain in only a small number of adult RGCs, indicating that mTOR signaling is down-regulated in the majority of adult RGCs. These changes correlate with the decrease in the overall axonal growth abilities as these neurons mature.

We next sought to determine why the subset of adult RGCs with p-S6 signals still cannot regenerate their injured axons. It has been previously reported that upon experiencing stresses such as hypoxia, cells respond by suppressing mTOR signaling (27-30), an evolutionally conserved stress response proposed to maintain energy homeostasis for survival. Thus, we postulated that stress(es) resulting from axotomy may reduce global translation in injured neurons. To test this, we estimated the rate of new protein synthesis in purified RGCs from control and injured rats. Control and injured RGCs were incubated with 35S-methanine/cysteine and the extracts from these cells were resolved using SDS-PAGE. 35S-methanine/cysteine incorporated proteins normalized against total protein contents were quantified, and the results showed a significant decrease in new protein synthesis in axotomized adult RGCs.

We next studied whether nerve lesion down-regulates the activity of the mTOR pathway by immunohistochemical analysis of retinal sections with anti-p-S6 antibodies. Our results indicate that axotomy almost completely abolished the remaining p-S6 signals in adult RGCs at all post-injury time points examined (1, 3, 7 days) in control mice, indicating that axotomy triggers a rapid and sustained down-regulation of mTOR mediated signals, and that antagonizing this down-regulation promotes regeneration. in wild type adult CNS neurons.

Previous work suggested that the up-regulation of stressed induced molecules Redd1/2 (regulated in development and DNA damage responses 1/2) may mediate the inhibition of mTOR in cells under stress (27-30). We thus analyzed Redd1/2 expression in injured neurons by quantitative real time PCR (q-PCR) using mRNAs derived from FACS-purified rat RGCs. No significant changes in Redd1/2 mRNA were found in axotomized RGCs. As a positive control, we found that the expression of Gadd45a, a gene known to be up-regulated after axotomy (31), is significantly increased in this same set of injury samples.

We next tested whether PTEN inhibition affects the p-S6 level in the adult RGCs both before and after injury. In the uninjured AAV-Cre injected PTENf/f mice, the percentage of anti-phospho-S6 stained RGCs was not significantly different from that in wild type or in AAV-GFP injected PTENf/f mice. However, the intensity of p-S6 signal appeared enhanced and these p-S6 positive RGCs showed increased cell size, consistent with previous studies of PTEN-deletion in other types of neurons (32, 33). Importantly, after optic nerve crush, similar percentages of p-S6 positive RGCs remained at 1, 3, or 7 days post-injury in the AAV-Cre injected PTENf/f mice. Thus, despite a stress response to axotomy, these axotomized neurons with PTEN deletion still possess the mTOR activity at the levels similar to uninjured wild type neurons. The percentage of regenerating fibers (8-10%) was similar to that of p-S6 positive axotomized RGCs (8-10%).

To further examine whether activation of the mTOR pathway is sufficient to promote axon regeneration, we performed similar optic nerve injury/regeneration assays using TSC1f/f conditional knockout mice (34). TSC1 and 2 form a protein complex which negatively regulates mTOR signaling (35-39). Previous reports indicated that loss of either TSC1 or TSC2 leads to constitutive activation of mTOR pathway (38). As expected, in AAV-Cre injected TSC1f/f mice, strong p-S6 signals were observed in axotomized RGCs, and there was a significant enhancement of RGC survival after injury. More importantly, considerable axon regeneration was observed in TSC1-deleted but not in wild type mice injected with AAV-Cre. The extent of axon regeneration in TSC1 deleted mice was slightly weaker than that induced by PTEN deletion, indicating that changes in other downstream targets of PTEN, such as Akt and GSK-3 activity (40, 41), may also be involved in regenerative growth. Nonetheless, these results indicate that activating the mTOR pathway is sufficient to promote both CNS neuron survival and axon regeneration.

Our results reveal that mTOR activity is suppressed in axotomized CNS neurons by a two-step down-regulation of the mTOR signaling; first by developmental maturation and second by axotomy-triggered stress response. Our results provide a new avenue to promote long distance CNS axon regeneration after injury, wherein increasing positive regulators of mTOR signaling, or inhibiting negative regulators of mTOR signaling (such as with chemical inhibitors of TSC1/2 or PTEN (42)), may be used transiently after CNS injury to prevent the down-regulation of protein synthesis and to promote axon regeneration and functional recovery.

EXAMPLE 2a

Pharmacological PTEN Inhibition Promotes Regeneration of Lesioned Optic Nerve Fibers in Adult Mice We designed a similar optic nerve study to demonstrate that pharmacological inhibitors of neuronal PTEN activity similarly promote axon regeneration, adapting a previously described model of optic nerve crushing [Fischer et al, J. Neurosci. 18, 1646 (2004)]. Adult mouse optic nerves are exposed behind the eyeball and crushed. Immediately after injury in adult mice, GELFOAM®, an absorabable gelatin powder, soaked in solutions of alternative PTEN inhibitors at serial concentrations (Table 1) or 0.1% DMSO (control) is placed against the crush site of the nerve and replaced every three days for the first six days of the study.

TABLE 1

PTEN inhibitor solutions

| PTEN Inhibitor | Concentrations |
| --- | --- |
| potassium bisperoxo(bipyridine)oxovanadate (V) (bpV(bipy)) | 10, 100, 1,000 ng/ml |
| dipotassium bisperoxo(5-hydroxypyridine-2-carboxyl)oxovanadate (V) (bpV(HOpic)) | 10, 100, 1,000 ng/ml |
| potassium bisperoxo(1,10-phenanthroline)oxovanadate (V), (bpV(phen)) | 10, 100, 1,000 ng/ml |
| dipotassium bisperoxo(picolinato)oxovanadate (V), (bpV(pic)) | 10, 100, 1,000 ng/ml |

Animals are sacrificed two weeks post injury followed by transcardial perfusion with 4% paraformaldehyde. Optic nerves are cryosectioned at 10 μm and stained with an anti-GAP43 antibody (Chemicon) to detect regenerating axons [Fischer et al, supra]. Little regeneration is detected in DMSO-treated control mice. However, injury site application of PTEN inhibitors results in significant increases in axonal regrowth and the number of regenerating axons, measured 0.25 mm beyond the injury site, compared to control mice.

EXAMPLE 2b

Pharmacological PTEN Inhibition Promotes Regeneration of Lesioned Optic Nerve Fibers in Adult Mice In subsequent similar experiments, we injected PTEN inhibitors of Table 2 into the retina, performed optic nerve injury, and found increased neuronal survival and axon regeneration.

TABLE 2

PTEN inhibitors

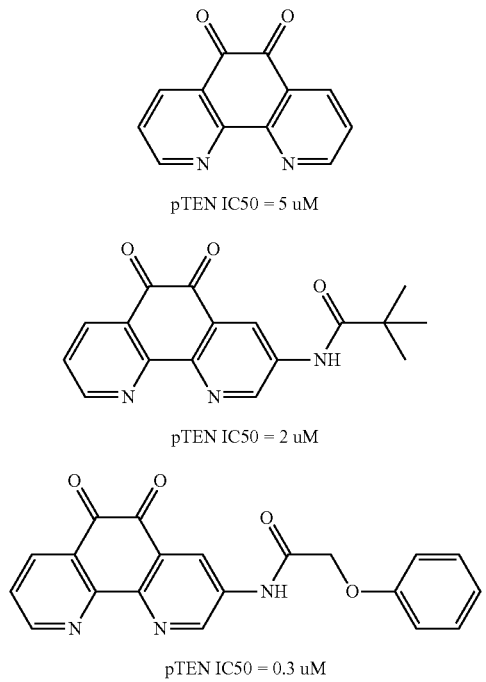

pTEN IC50 = 5 uM pTEN IC50 = 2 uM pTEN IC50 = 0.3 uM

EXAMPLE 3

Exemplary PTEN Inhibition Assays for General Screening and 1050 Determinations

PTEN inhibitors are evaluated in an inhibition assay conducted in half-volume 96 well plates in 25 ul total volume per well containing 2 mM dithiothreitol (DTT) and 0.1 mM Tris buffer, pH 8.0 and up to 3 ug total protein of PTEN. Small volumes of the test inhibitor candidates (stock concentrated solutions of 25 mM in DMSO) are mixed with the PTEN solution at room temperature for about 10 minutes and then substrate is added. The reaction mix is then incubated in 37° C. for 20 minutes. Subsequent to this a 100 ul aliquot of malachite green buffer (Upstate, Charlottesville, Va.) is added to develop the color in the dark at room temperature (this solution also stops the dephosphorylation reaction). A SpectraMax Plus spectrophotometric plate reader (Molecular Devices, Sunnyvale, Calif.) is used to measure the optical density at 650 nanometers.

The initial screening concentration of inhibitor candidates is 250 uM and candidates with inhibition greater than 50% compared with a no-inhibitor control group are then evaluated further to determine IC50 values. PTEN can be purchased commercially or prepared by literature methods [i.e. from cell extracts of bacteria expressing genetic reconstituted Glutathione-S-transferase (GST)-PTEN fusion protein whereupon the GST-PTEN in the cell extract is bound onto and purified from Glutathione Sepharose 4B gel (Amersham, Piscataway, N.J.)]. Suitable PTEN reaction substrates include (a) PIP3 Phospholipid vesicle (PLV), which may be made using published methods (Maehama et al. 2000, Analytical Biochemistry 279, 248-250) and is typically utilized at about 50 uM in the final reaction mixture (based on component concentration), (b) water soluble PIP3 Echelon Biosciences, Salt Lake City, Utah, utilized at a working concentration of 100 uM, and (c) phosphorylated poly glutamic-tyrosine peptide designated (EEEEYp)n, where n=2 or 3 (Biofacilities of Indiana University, Indianapolis, Ind.), wherein a working concentration of the phosphorylated tyrosine substrate is 200 uM.

To determine the dose response of potential PTEN inhibitors, doses of test compounds ranging from 1 nM to 250 uM (final reaction mix concentrations) are evaluated in the general PTEN inhibition assay (supra). To obtain performed IC50 data, two separate rounds of the dose response assay are performed. In the first round, PTEN activity is tested in the presence of inhibitor at 10 fold serial dilutions ranging from 1 nM to 250 uM. Once the concentration range is determined, at which PTEN activity changes dramatically, two additional concentration data points within this range are added and the PTEN inhibition assay is then rerun for the second round. The PTEN inhibition IC50 is presented as the inhibitor concentration at which 50% of the PTEN activity (measured by phosphate production and compared to un-inhibited control samples) is found. The IC50 determination from the data is made using Prism software (GraphPad Software, San Diego, Calif.).

EXAMPLE 4

PTEN Inhibition Promotes Axonal Regeneration after Spinal Injury in Rats

This animal study demonstrates that in an animal model for spinal injury, axonal regeneration can be promoted by intrathecal or intravenous administration of PTEN inhibitors bpV (bipy), bpV(HOpic), bpV(phen) and bpV(pic). Methodology for this animal study was adapted from Nash et al (J. Neurosci (2002) 22:7111-7120), Luo et al (Molecular Pain (2005) 1:29), and Obata et al (J. Neurosci. (2004) 24:10211-22).

Adult Sprague Dawley rats (300-400 gm) are trained and tested in a directed forepaw reaching (DFR) apparatus which measures grasping ability. The apparatus, which is described in detail by Nash et al., supra, is a box that consists of two compartments: a main compartment for housing the rats and a minor compartment for the food, separated by a PLEXIGLASS® divider. The minor compartment is subdivided into slots of equal size, each holding a pellet of food. Between the slots and the PLEXIGLASS® there is a gap. The apparatus is configured such that in order to retrieve a food pellet from a slot, a rat must extend a forelimb through a hole in the PLEXI- GLASS® divider, and grasp the pellet and lift it over the gap and out of the slot. If the rat merely rakes the food in the slot towards the hole in the PLEXIGLASS®, the food will drop from the slot into the gap and fall to the floor of the minor compartment. The floor of the minor compartment can be configured to allow a rat to retrieve food that drops or it can be lowered to prevent the rat from reaching dropped food. Prior to inducing spinal injury, the rats are food restricted, receiving ~3 gm food/100 gm body weight per day, before and throughout training and testing. Weight is monitored to ensure that rats are reduced to no less than 80% of their original body weight at any time. All rats are given shaping periods for 2-3 d in the box to allow them to learn the task while they become familiar with the testing situation. Animals are trained twice per day for 5 d and then tested twice per day for 5 d, and presurgical DFR data is collected. During the testing period, rats are given 5 min to complete the task and are allowed to make as many attempts as they want during this time period. Rats are required to return to at least 95% of their original weight to ensure that they are healthy before undergoing surgery.

Rats are randomly assigned to control or experimental groups. Sham control rats undergo surgical procedure without lesioning, and with or without placement of a mini osmotic pump (Alzet type 2001; Durect, Cupertino, Calif.). Lesioned control rats receive no treatment, tail vein injection with vehicle only treatment, insertion of a mini osmotic pump only treatment, or insertion of a mini osmotic pump with vehicle only treatment. After anesthesia with isoflurane, the rats are placed on an operating board in such a way as to bend the cervical spinal cord for maximum exposure. A laminectomy is performed exposing the dorsum of the spinal cord between C2 and C4. The dorsal columns are identified bilaterally, and, in all rats except for those in the sham group, a suture needle is passed through the spinal cord, isolating the dorsal funiculus. The suture thread is gently lifted, and a pair of iridectomy scissors is used to bilaterally transect the dorsal funiculus, thereby transecting the dorsal corticospinal tract (CST). Visualization of the dorsal horns and the central gray commissure confirms accuracy of the lesion borders. A pledget of biodegradable GELFOAM®, an absorabable gelatin powder, soaked in a fluorescent retrograde tracer, FLUOROGOLD™ (3% in 0.9% saline; Molecular Probes), is placed in the lesion site to identify the neurons whose axons are transected, confirming the lesion. Rats designated for PTEN inhibitor treatment or corresponding control treatment are implanted with mini osmotic pumps adjacent to the lesion site. The pumps in the treatment group operate at a rate of 1 μl/hr for a period of 7 days and are filled with PTEN inhibitor (bpV(bipy), bpV(HOpic), bpV(phen) or bpV(pic)) at a concentration of 500 ng/μl. The overlying muscles and skin are sutured, and the rats are placed on a heating pad to maintain body temperature. Each rat receives a single dose of buprenorphine (0.1 mg/kg) immediately after surgery to alleviate pain.

One hour after the spinal cord is lesioned, the rats in the tail vein injection treatment group receive a bolus injection of 100 μg/kg PTEN inhibitor (bpV(bipy), bpV(HOpic), bpV(phen) or bpV(pic)) in a saline/DMSO vehicle. The treatment is repeated every 24 hours on days 1 through 7 post-lesion. Vehicle only control rats undergo the same treatment but are injected with an equal volume of saline/DMSO in a tail vein.

Rats are trained twice per week during weeks 2-5 after surgery. Some rats may be profoundly impaired such that they may not be able to grasp food in the DFR task in the early postsurgical period. In this case, the apparatus can be configured to allow the rats to rake food into the main compartment that drops from the slot onto the floor of the minor compartment (see Nash et al., supra). This ensures that the reaching portion of the DFR task does not extinguish. The severity of the grasping impairment decreases as the postsurgical period increases, and the configuration of the apparatus that does not permit food raking can be gradually reestablished. By the end of the postsurgical recovery period, all rats are able to successfully perform the DFR task, to some degree. During the sixth week after surgery, rats are tested twice per day for 5 d, and postsurgical DFR data is collected by a blinded investigator. Just as during the presurgery testing period, the rats are allowed 5 min to complete the task during the postsurgery testing period and are allowed to make as many attempts as they want during this time period. The data is collected in terms of total number of attempts and percentage of successful attempts. An attempt is scored only when a rat reaches into a slot and displaces the pellet or drops it to the floor of the minor compartment. A successful attempt is scored when a rat grasps a pellet, lifts it over the gap and pulls it through the PLEXIGLASS® divider into the main portion of the testing apparatus.

Sham animals perform the DFR task as well postsurgically as they do presurgically, demonstrating that only the lesion, and no other portion of the surgical procedure, inhibits the rats' abilities to perform the DFR task. The lesion and vehicle groups are the most impaired of all of the groups after surgery. The lesion and vehicle groups are able to perform the DFR task with a success rate of only about 40%. Significantly better performance by the SP600125-treated group demonstrates the effect of the treatment on functional recovery after spinal injury.

Seven weeks after injury, rats are prepared for injection of biotin dextran tetramethylrhodamine (BDT; Molecular Probes). This fluorescent anterograde tracer, injected into the primary motor cortex, is used to label CST axons caudal to the lesion site in the spinal cord. After anesthesia with isoflurane (5%), rats are placed in a stereotaxic instrument, and a total of six stereotaxically determined holes (0.9 mm diameter) are drilled in the skull over the primary motor cortices associated with the forelimbs. The anteroposterior (AP) and mediolateral (ML) coordinates for these injections, from bregma, are as follows: ±0.5 AP and ±3.5 ML; ±1.5 A/P and ±2.5 ML; and ±2.5 AP and ±1.5 ML. All injections are delivered at a depth of 2.5 mm from the surface of the skull. A 10 μl Hamilton syringe is used to inject BDT bilaterally into layer V of the cortex. Three injections into each cortical hemisphere are used to administer a total of 1.2 μl of the anterograde tracer. Bone wax (Ethicon, Somerville, N.J.) is used to seal the holes in the skull, the scalp is sutured, and a single dose of buprenorphine (0.1 mg/kg) is administered immediately after surgery to alleviate pain. Rats are killed 3 d after tracer injections.

Seven weeks and 3 d after lesioning, rats are anesthetized with chloral hydrate (10 ml/kg) and perfused transcardially with 300 ml of PBS, pH 7.4, followed by 300 ml of 4% paraformaldehyde in 0.1 M phosphate buffer. After the animals are killed, all brains and spinal cords are removed and soaked overnight in 30% sucrose in a 0.1M phosphate buffer solution. The brains are cut coronally and the spinal cords are cut horizontally at a thickness of 20 μm with a freezing microtome and mounted on PROBEON™ (Fisher Scientific, Pittsburgh, Pa.) coated slides. Brain and spinal cord sections are examined using a Nikon (Tokyo, Japan) Labophot fluorescent microscope, and images are captured using a digital still camera. The forelimb representation of the primary motor cortex is identified based on the stereotaxic BDT injection sites. The primary motor cortex is examined in all rats. Presence of FLUOROGOLD™-labeled neurons in layer V of the primary motor cortex, confirms that the dorsal CST axons were transected during the lesioning procedure. Because all CST axons located in the dorsal funiculus are transected during surgery and not just those in the forelimb representation, FLUOROGOLD™-labeled neurons are found throughout the primary motor cortex in layer V. The only exception to this labeling pattern is in the brains of the rats in the sham group whose brains have no FLUOROGOLD™ label.

The spinal cord caudal to the lesion is examined, and the BDT-labeled axons occupying the region of the spinal cord normally occupied by the dorsal CST are counted. For each section, the number of BDT-labeled axons is counted at 3 mm intervals caudal to the lesion, beginning 1 mm distal to the injury (i.e., 1 mm, 4 mm, 7 mm, etc.) and ending 19 mm caudal to the lesion site. Innervation of the rat forepaw extends to T1, a distance of 15.1 mm from the lesion at C3. Therefore, analysis of the axons out to 19 mm caudal to the lesion ensures that the entire distance representing the forepaw is examined. At each interval, the total number of BDT-labeled axons (left and right CST combined) along a 500 μm length (length of microscope field) is counted. In each field counted, the focal plane is adjusted up and down to ensure that a single continuous axon is not double counted if it traverses out of the focal plane and reemerges farther down in the same field. The number of BDT-labeled axons present is examined for control and experimental groups at each of the distances (i.e. 1, 4, 7 . . . and 19 mm caudal to the lesion site). Throughout all of the examined intervals, the mean number of axons is highest in the sham group, and, at each distance examined, the mean number of labeled axons in the sham group is significantly higher than in the other groups. No significant difference is observed between the means of the lesion and vehicle groups at any distance examined. In these groups, axons are found only a short distance caudal to the injury, and, by 10 mm distal to the lesion to the farthest distance examined, all of the tissue is virtually devoid of axons. Significantly more labeled axons at each distance in the PTEN inhibitor-treated group compared to lesioned control rats demonstrates that this treatment promotes axonal regeneration after spinal injury.

EXAMPLE 5

Improved Neurological Outcome Following PTEN Inhibitor Treatment for Acute Spinal Cord Injury We adapted our protocol for this study from the Sygen® Multicenter Acute Spinal Cord Injury Study described by Geisler et al (Spine (2001) 26:587-598). It is a prospective, double-blind, randomized, and stratified multicenter trial, randomizing approximately 800 patients so as to have at least 720 completed and evaluable in each treatment group: placebo, low-dose PTEN inhibitor (bpV(bipy), bpV(HOpic), bpV(phen) or bpV(pic)), and high-dose PTEN inihibitor. The patients are stratified into six groups, according to three degrees of injury severity (American Spinal Injury Association grades A, B, and C+D) and two levels of anatomic injury (cervical and thoracic). The trial is sequential with pre-planned interim analyses as each group of 720/4=180 patients reach their 26-week examination and become evaluable. Patients are required to have at least one lower extremity with a substantial motor deficit. Patients with spinal cord transection or penetration are excluded, as are patients with a significant cauda equina, brachial or lumbosacral plexus, or peripheral nerve injury. Gunshot injuries that do not penetrate the cord are allowed. Multiple trauma is allowed as long as it is not so severe as to prevent neurologic measurement evaluation or interpretation.

All patients are to receive the second National Acute Spinal Cord Injury Studies (NASCIS II) dose regimen of methylprednisolone (MPSS) starting within 8 hours after the spinal cord injury (SCI). To avoid any possible untoward interaction between MPSS and PTEN inhibitors the study medication is not started until after completion of MPSS administration.

The placebo group has a loading dose of placebo and then 56 days of placebo. The low dose PTEN inhibitor group has a 50-mg loading dose administered intravenously (i.v.) followed by 10 mg/day i.v. for 56 days. The high dose PTEN inhibitor group has a 250-mg loading dose followed by 50 mg/day for 56 days.

The baseline neurologic assessment includes both the AIS and detailed American Spinal Injury Association (ASIA) motor and sensory examinations. Modified Benzel Classification and the ASIA motor and sensory examinations are performed at 4, 8, 16, 26, and 52 weeks after injury. The Modified Benzel Classification is used for post-baseline measurement because it rates walking ability and, in effect, subdivides the broad D category of the AIS. Because most patients have an unstable spinal fracture at baseline, it is not possible to assess walking ability at that time; hence the use of different baseline and follow-up scales. Marked recovery is defined as at least a two-grade equivalent improvement in the Modified Benzel Classification from the baseline AIS. The primary efficacy assessment is the proportion of patients with marked recovery at week 26. The secondary efficacy assessments include the time course of marked recovery and other established measures of spinal cord function (the ASIA motor and sensory scores, relative and absolute sensory levels of impairment, and assessments of bladder and bowel function).

EXAMPLE 6

Effect of PTEN Inhibition after Cortical Impact Injury in Rats

We adapted methodology from Cherian et al. (J Pharmacol Exp Ther. (2003) 304:617-23), to test the effects of different doses and treatment schedules of PTEN inhibitors on a rat model of brain impact injury. A total of 60 male Evans rats weighing 300 to 400 g are assigned to one of the following doses injected intraperitoneally (i.p.) or intracerebral ventricularly (i.c.v.): none (saline control group), 0.01, 0.1, 1.0, and 10.0 mg/kg/day PTEN inhibitors (bpV(bipy), bpV(HOpic), bpV(phen) or bpV(pic)). The rats are further assigned to a treatment duration of 1, 3, 7, or 14 days, with 4 rats in each treatment group, and 3 rats in each control group (i.e. saline administered for 1, 3, 7, or 14 days).

The details of the methods to produce the impact injury have been previously described (Cherian et al., J. Neurotrauma (1996) 13:371-383). Briefly, the head of the rat is fixed in a stereotaxic frame by ear bars and incisor bar. A 10-mm diameter craniotomy is performed on the right side of the skull over the parietal cortex. An impactor tip having a diameter of 8 mm is centered in the craniotomy site perpendicular to the exposed surface of the brain at an angle of approximately 45 degrees to the vertical. The tip is lowered until it just touches the dural surface. The impactor rod is then retracted, and the tip advanced an additional 3 mm to produce a brain deformation of 3 mm during the impact. Gas pressure applied to the impactor is adjusted to 150 psi, giving an impact velocity of approximately 5 m/s and duration of approximately 150 to 160 ms.

Rats are fasted overnight and anesthetized with 3.5% isoflurane in 100% oxygen in a vented anesthesia chamber. Following endotracheal intubation with a 16-gauge Teflon catheter, the rats are mechanically ventilated with 2% isoflurane in 100% oxygen for the surgical preparation and for the impact injury. Intracranial pressure (ICP) is monitored by a 3F microsensor transducer (Codman & Schurtleff, Randolph, Mass.) inserted in the left frontal lobe, well away from the impact site. ICP is monitored during the impact injury as a measure of the severity of the injury. Rectal temperature is maintained at 36.5-37.5° C. by a heating pad, which is controlled by rectal thermistor. Brain temperature is kept constant at 37° C. with the help of a heating lamp directed at the head.

The rats that are to receive i.c.v. administration of PTEN inhibitors receive mini-pump implants using procedures described by Kitamura et al (J Pharmacol Sci (2006) 100:142-148). Briefly, the rats are fixed in a stereotaxic frame (David Kopf Instruments, Tujunja, Calif.). Guide cannulae are implanted into the left lateral ventricle (Bregma −0.8 mm, lateral 1.5 with a depth of 3.7 mm below the dura). Each cannula is then connected by a catheter to an ALZET® mini-osmotic pump implanted subcutaneously in the scapular region and configured to continuously infuse the drug to achieve the specified daily dose of AS601245 (or vehicle only for control groups).

For rats in the i.p. treatment group, each dose of PTEN inhibitor is dissolved in 1 ml of sterile 0.9% saline so that the volume delivered is the same for each group and only the dosage of PTEN inhibitor varies. The first dose is administered within 1 hour following impact injury. And once daily thereafter for the assigned treatment duration.

After removing all catheters and suturing the surgical wounds, the rats are allowed to awaken from anesthesia. For the first 3 days post injury, the rats are treated with butorphanol tartrate, 0.05 mg of i.m. every 12 h (twice a day), for analgesia and enrofloxacin 2.27%, 0.1 ml of IM qd, to reduce the risk of postoperative infections.

The outcome measures are performed by investigators who are blinded to the treatment group. At 2 weeks after the impact, the animals are deeply anesthetized with a combination of ketamine/xylazine/acepromazine and perfused transcardially with 0.9% saline, followed by 10% phosphate buffered formaldehyde. The entire brain is removed and fixed in 4% formalin. The fixed brains are examined grossly for the presence of contusion, hematoma, and herniation. The brains are photographed, sectioned at 2-mm intervals, and then embedded in paraffin. Hematoxylin and eosin (H&E) stained 9-um thick sections are prepared for histologic examination. Particular care is made to include the largest cross-sectional area of cortical injury on the cut surface of the embedded sections. The H&E-stained coronal sections are digitized using a POLAROID® Sprint Scanner (POLAROID® Corporation, Waltham, Mass.) equipped with a PATHSCAN™ Enabler (Meyer Instruments, Houston, Tex.). The injury volume is measured by determining the cross-sectional area of injury in each H&E-stained coronal image and multiplying by the thickness of the tissue between the slices. This slab volume technique is implemented on the image processing program Optimas 5.2 (Optimas Corporation, Seattle, Wash.). Neurons in the middle 1-mm segments of the CA1 and CA3 regions of the hippocampus are counted at a magnification of 200×. Neurons are identified by nuclear and cytoplasmic morphology, and individual cells are counted whether normal or damaged. Neurons with cytoplasmic shrinkage, basophilia, or eosinophilia or with loss of nuclear detail are regarded as damaged. The regions measured are 1 mm long and 1 mm wide (0.5 mm on either side of the long axis of the segment). The total number of neurons and the number of neurons that appear normal are expressed as neurons per squared millimeter.

EXAMPLE 7

PTEN Inhibition Promotes Neural Regeneration in Animal Models of Focal Brain Ischemia This study uses previously described methods (Brines et al, Proc Natl Acad Sci USA. (2000) 97:10526-31) to demonstrate the effect of systemically administered PTEN inhibitors in an animal model of focal brain ischemia. Sprague-Dawley male rats weighing ~250 g are anesthetized with pentobarbital [60 mg/kg body weight (BW)]. Body core temperature is thermostatically maintained at 37° C. by using a water blanket and a rectal thermistor (Harvard Apparatus) for the duration of the anesthesia. The carotid arteries are visualized, and the right carotid is occluded by two sutures and cut. A burr hole adjacent and rostral to the right orbit allows visualization of the MCA, which is cauterized distal to the rhinal artery. Animals are then positioned on a stereotaxic frame. To produce a penumbra surrounding this fixed MCA lesion, the contralateral carotid artery is occluded for 1 h by using traction provided by a fine forceps. 0.5 ml of a 1 µg/ml solution of PTEN inhibitor (bpV(bipy), bpV(HOpic), bpV (phen) or bpV(pic)) or vehicle control is administered at 1 hr, 1 day, 5 days, or 10 days from the onset of the reversible carotid occlusion. To evaluate the extent of injury, the animals are killed after 15 days, the brains are removed, and serial 1-mm thick sections through the entire brain are cut by using a brain matrix device (Harvard Apparatus). Each section is then incubated in a solution of 2% triphenyltetrazolium chloride (wt/vol) in 154 mM NaCl for 30 min at 37° C. and stored in 4% paraformaldehyde until analysis. Quantification of the extent of injury is determined by using a computerized image analysis system (MCID, Imaging Research, St. Catharine's, ON, Canada). To accomplish this, a digital image of each section is obtained and the area of injury delineated by outlining the region in which the tetrazolium salt is not reduced, i.e., nonviable tissue. For cases in which the necrosis is so severe that tissue is actually lost and therefore the borders can not be directly assessed, an outline of the contralateral side is used to estimate the volume of injured brain. Total volume of infarct is calculated by reconstruction of the serial 1-mm thick sections.

REFERENCES

1. J. W. Fawcett, Trends Neurosci 15, 5 (January 1992).
2. M. T. Filbin, Philos Trans R Soc Lond B Biol Sci 361, 1565 (Sep. 29, 2006).
3. M. T. Fitch, J. Silver, Exp Neurol 209, 294 (February 2008).
4. J. L. Goldberg, M. P. Klassen, Y. Hua, B. A. Barres, Science 296, 1860 (Jun. 7, 2002).
5. M. E. Schwab, D. Bartholdi, Physiol Rev 76, 319 (April 1996).
6. L. C. Case, M. Tessier-Lavigne, Curr Biol 15, R749 (Sep. 20, 2005).
7. G. Yiu, Z. He, Nat Rev Neurosci 7, 617 (August 2006).
8. A. J. Aguayo et al., J Exp Biol 153, 199 (October 1990).
9. L. Benowitz, Y. Yin, Exp Neurol 209, 389 (February 2008).
10. N. Gogolla, I. Galimberti, P. Caroni, Curr Opin Neurobiol 17, 516 (October 2007).
11. R. A. Weinberg, In the biology of cancer. R. A. Weinberg, Ed. (Garland Science, 2007), pp. 209-253.

12. S. Marino, M. Vooijs, H. van Der Gulden, J. Jonkers, A. Berns, Genes Dev 14, 994 (Apr. 15, 2000).
13. X. Yang, C. Li, P. L. Herrera, C. X. Deng, Genesis 32, 80 (February 2002).
14. B. D. Harfe, M. T. McManus, J. H. Mansfield, E. Hornstein, C. J. Tabin, Proc Natl Acad Sci USA 102, 10898 (Aug. 2, 2005).
15. N. Bardeesy et al., Nature 419, 162 (Sep. 12, 2002).
16. M. Groszer et al., Science 294, 2186 (Dec. 7, 2001).
17. J. Bertrand, M. J. Winton, N. Rodriguez-Hernandez, R. B. Campenot, L. McKerracher, J Neurosci 25, 1113 (Feb. 2, 2005).
18. M. Bahr, Trends Neurosci 23, 483 (October 2000).
19. J. L. Goldberg et al., Neuron 33, 689 (Feb. 28, 2002).
20. I. Selles-Navarro, B. Ellezam, R. Fajardo, M. Latour, L. McKerracher, Exp Neurol 167, 282 (February 2001).
21. M. Cully, H. You, A. J. Levine, T. W. Mak, Nat Rev Cancer 6, 184 (March 2006).
22. D. A. Guertin, D. M. Sabatini, Cancer Cell 12, 9 (July 2007).
23. N. Hay, N. Sonenberg, Genes Dev 18, 1926 (Aug. 15, 2004).
24. J. Luo, B. D. Manning, L. C. Cantley, Cancer Cell 4, 257 (October 2003).
25. D. C. Fingar, J. Blenis, Oncogene 23, 3151 (Apr. 19, 2004).
26. D. H. Kim et al., Cell 110, 163 (Jul. 26, 2002).
27. J. Brugarolas et al., Genes Dev 18, 2893 (Dec. 1, 2004).
28. M. N. Corradetti, K. Inoki, K. L. Guan, J Biol Chem 280, 9769 (Mar. 18, 2005).
29. J. H. Reiling, E. Hafen, Genes Dev 18, 2879 (Dec. 1, 2004).
30. A. Sofer, K. Lei, C. M. Johannessen, L. W. Ellisen, Mol Cell Biol 25, 5834 (July 2005).
31. D. Fischer, V. Petkova, S. Thanos, L. I. Benowitz, J Neurosci 24, 8726 (Oct. 6, 2004).
32. S. A. Backman et al., Nat Genet 29, 396 (December 2001).
33. C. H. Kwon et al., Neuron 50, 377 (May 4, 2006).
34. L. Meikle et al., J Neurosci 27, 5546 (May 23, 2007).
35. A. Garami et al., Mol Cell 11, 1457 (June 2003).
36. K. Inoki, T. Zhu, K. L. Guan, Cell 115, 577 (Nov. 26, 2003).
37. L. J. Saucedo et al., Nat Cell Biol 5, 566 (June 2003).
38. A. R. Tee, B. D. Manning, P. P. Roux, L. C. Cantley, J. Blenis, Curr Biol 13, 1259 (Aug. 5, 2003).
39. Y. Zhang et al., Nat Cell Biol 5, 578 (June 2003).
40. D. A. Cross, D. R. Alessi, P. Cohen, M. Andjelkovich, B. A. Hemmings, Nature 378, 785 (Dec. 21-28, 1995).
41. W. Y. Kim et al., Neuron 52, 981 (Dec. 21, 2006).
42. E. Rosivatz et al., ACS Chem Biol 1, 780 (Dec. 15, 2006).
43. S. G. Leaver et al., Gene Ther 13, 1328 (September 2006).
44. K. Park, J. M. Luo, S. Hisheh, A. R. Harvey, Q. Cui, J Neurosci 24, 10806 (Dec. 1, 2004).

The foregoing examples and detailed description are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims

What is claimed is:

1. A method for promoting survival of, or axon regeneration in a lesioned mature neuron in situ, comprising contacting the lesioned neuron with a therapeutically effective amount of a PTEN inhibitor, to thereby promote survival of, or axon regeneration in the neuron, wherein the lesion results from acute spinal cord injury.

2. The method of claim 1, further comprising detecting the resultant promotion of the survival of, or axon regeneration in the neuron.

3. The method of claim 2, wherein the detecting step is by an indirect assay of axon regeneration.

4. The method of claim 2, wherein the detecting step is by a direct assay of axon regeneration.

5. The method of claim 1, wherein the inhibitor is administered locally at the neuron.

6. A method for promoting survival of, or axon regeneration in a lesioned mature neuron in situ, comprising contacting the lesioned neuron with a therapeutically effective amount of a PTEN inhibitor, to thereby promote survival of, or axon regeneration in the neuron, wherein the lesioned neuron is in the spinal cord.

7. The method of claim 6, further comprising detecting the resultant promotion of the survival of, or axon regeneration in the neuron.

8. The method of claim 7, wherein the detecting step is by an indirect assay of axon regeneration.

9. The method of claim 7, wherein the detecting step is by a direct assay of axon regeneration.

10. The method of claim 6, wherein the inhibitor is administered locally at the neuron.

* * * * *

UNITED STATES PATENT AND TRADEMARK OFFICE
CERTIFICATE OF CORRECTION

PATENT NO. : 8,728,756 B2
APPLICATION NO. : 13/729091
DATED : May 20, 2014
INVENTOR(S) : Zhigang He et al.

Page 1 of 1

It is certified that error appears in the above-identified patent and that said Letters Patent is hereby corrected as shown below:

In the Specification

Column 1, Lines 20-22:
"This invention was made with government support under grant PO30-HD18655 awarded by the National Institutes of Health. The government has certain rights in the invention." should be replaced with -- This invention was made with government support under Grant number NS051788, awarded by The National Institutes of Health. The government has certain rights in the invention. --

Signed and Sealed this
Sixteenth Day of March, 2021

Drew Hirshfeld
*Performing the Functions and Duties of the
Under Secretary of Commerce for Intellectual Property and
Director of the United States Patent and Trademark Office*